United States Patent [19]  [11] 4,151,348
Traeger et al.  [45] Apr. 24, 1979

[54] CRYSTALLIZED POTASSIUM SALT OF ADENOSINE-5-DIPHOSPHORIC ACID AND METHOD OF PREPARING SAME

[75] Inventors: Heinrich Traeger, Penzberg; Herbert Brustmann; Erich Haid, both of Tutzing, all of Fed. Rep. of Germany

[73] Assignee: Boehringer Mannheim GmbH, Mannheim-Waldhof, Fed. Rep. of Germany

[21] Appl. No.: 837,341

[22] Filed: Sep. 28, 1977

[30] Foreign Application Priority Data

May 18, 1977 [DE] Fed. Rep. of Germany ....... 2722644

[51] Int. Cl.$^2$ .................... C07H 17/00; A61K 31/70
[52] U.S. Cl. ...................................... 536/27; 536/28; 424/180
[58] Field of Search .......................................... 536/27

[56] References Cited

U.S. PATENT DOCUMENTS

| | | | |
|---|---|---|---|
| 1,978,881 | 10/1934 | Lautenschlager | 536/27 |
| 2,700,038 | 1/1955 | Lipton et al. | 536/27 |
| 3,803,125 | 4/1974 | Bergmeyer et al. | 536/27 |

Primary Examiner—Johnnie R. Brown
Assistant Examiner—Blondel Hazel
Attorney, Agent, or Firm—Sprung, Felfe, Horn, Lynch & Kramer

[57] ABSTRACT

Crystalline orthorhombic potassium adenosine-5'-diphosphate having the space group $P2_12_12$ and the elemental cell constants $a = 28.53 \pm 0.03$ Å

$b = 10.49 \pm 0.02$ Å

$c = 6.33 \pm 0.02$ Å

$\alpha = \beta = \gamma = 90.0°$

Volume = 1894.4 Å$^3$, has superior stability, relative to conventional salt forms thereof, e.g., the disodium salt.

1 Claim, No Drawings

CRYSTALLIZED POTASSIUM SALT OF ADENOSINE-5-DIPHOSPHORIC ACID AND METHOD OF PREPARING SAME

The invention relates to a crystallized potassium salt of adenosine-5'-diphosphoric acid and a method for the preparation thereof.

Adenosine-5'-diphosphoric acid (ADP) occurs naturally as an intermediate product in fermentation processes, and also forms in muscle from ATP under the action of adenosine triphosphatase. ADP is widely used for scientific purposes as a starting substance for the synthesis of ATP and as a component of reagent compositions, especially for clinical diagnosis.

The hitherto known forms of ADP, which is used substantially in the form of its salts, are amorphous and are not sufficiently stable. That is, they have a tendency to decompose with the formation of adenosine monophosphate (AMP) and adenosine triphosphate (ATP). For example, when disodium ADP in amorphous form is stored for three weeks at 33° C., 10% of AMP and more than 3% of ATP are formed. This instability is a considerable disadvantage, especially in the reagent compositions mentioned above.

There exists, consequently, a need for a more stable form of ADP.

It has now been found that it is possible to produce a crystallized monopotassium salt of ADP of superior stability.

The invention provides crystalline, orthorhombic potassium salt of adesnosine-5'-diphosphoric acid having the space group $P2_12_12$ and the elemental cell constants $a = 28.53 \pm 0.03$ Å, $b = 10.49 \pm 0.02$ Å, $c = 6.33 \pm 0.02$ Å, $\alpha = \beta = \gamma = 90.0°$, volume $= 1894.4$ Å$^3$.

The determination of these values was made each from four reflex spacings on precision film using nickel filtered CuK$_\alpha$ radiation ($\lambda = 1.54182$ Å) at a film-to-crystal distance of 75.0 mm. According to the analysis it is a monopotassium salt dihydrate.

In Nature 262, 234 to 236 (1976) a crystallized rubidium salt of ADP is disclosed. This crystallized salt, however, is not known to have a superior stability, and it is furthermore stated in that publication that it had not been possible to crystallize other monovalent or divalent ADP salts.

The superior stability of the crystallized salt of the invention in comparison to the commercial amorphous ADP-Na$_2$ salt is shown by the following table.

|  | After preparation | | | After 1 week at +33° C. | | |
|---|---|---|---|---|---|---|
|  | ADP | AMP | ATP | ADP | AMP | ATP |
| Amorphous ADP-Na$_2$ | 86.9 | 1.7 | 0.56 | 79.6 | 5.9 | 2.3 |
| Cryst. ADP-K | 87.7 | 0.25 | 0.09 | 89.4 | 0.29 | 0.09 |

|  | After 2 wks at +33° C. | | | After 3 wks. at +33° C. | | |
|---|---|---|---|---|---|---|
|  | ADP | AMP | ATP | DP | AMP | ATP |
| Amorphous ADO-Na-hd 2 | 75.2 | 9.4 | 2.9 | 72.5 | 10.0 | 3.3 |
| Cryst. ADP-K | 89.2 | 0.35 | 0.11 | 88.3 | 0.72 | 0.07 |

The numerical values given in the above table are percentages determined analytically.

It can be seen from these figures that, in the accelerated aging test, the crystallized salt of the invention is subject to virtually no decomposition, whereas in the case of the known amorphous sodium salt a very obvious decomposition takes place.

An additional aspect of the invention is a method of preparing the crystalline potassium salt of ADP. This method consists in transforming adenosine-5'-diphosphoric acid in the form of the free acid or of one of its salts to a dilute aqueous solution of the potassium salt and, at a pH of 1.4 to 6, preferably 2.7 to 2.9, adding a water-soluble organic solvent until the onset of turbidity, stirring until crystallization starts, and isolating the crystals after crystallization ends, or it consists in mixing concentrated solutions of the free acid and an easily soluble potassium salt and separating the directly forming crystallizate. Crystallization can also be accomplished without stirring, although a considerably greater amount of time is then required for the residual crystallization.

It is preferable to use methanol as the hydrophilic organic solvent, in a ratio of the ADP-K solution to the solvent of 1:0.2 to 4, preferably 1:0.8 to 2, proceed at constant temperature until crystallization starts, and then lower the temperature to about 0° C. to 4° C. until crystallization is complete. Room temperature is preferred as the constant temperature.

In general, the aqueous ADP-K solution has a concentration prior to the crystallization of 1 to 35%, preferably of 8 to 12%.

In the method of the invention, the following can also be used as hydrophilic solvents: low alkanols, such as ethanol and propanol, ethers such as dioxane, nitriles such as acetonitrile, and ketones such as acetone, and mixtures of the named solvents.

The hydrophilic organic solvents used have to be sufficiently miscible in water, so that a homogeneous water-solvent-mixture system can be obtained for the crystallization of ADP-K.

Ordinarily, the crystallization will have ended substantially in two to forty hours after the onset of crystallization, although this will depend on the nature and amount of the impurities present in the solution, on the nature of the water-soluble organic solvents, and on the temperature and other such factors. The addition of seed crystals is advantageous in accelerating crystallization, especially when relatively large amounts of impurities are present in the solutions, such as AMP or ATP.

In addition to the method described above, the crystalline salt of ADP of the invention can also be obtained from pure water if the aqueous solution is let stand for a period of time at a concentration of 30 to 100%, although this will result in greater losses of yield. By the invention crystals are created which are characterized by a greater purity, much better stability, and no hygroscopicity, in contrast to the formerly known amorphous forms of ADP, such as ADP-Na$_2$ or ADP free acid.

Another possibility of obtaining crystalline ADP-K consists in adding to an aqueous solution of ADP (free acid) the stoichiometric amount of KCl or other such potassium salt. The crystalline ADP-K thus produced will have a higher content of water of crystallization.

The following examples will further illustrate the invention:

EXAMPLE 1

10 g of ADP free acid (99%) is dissolved in 70 ml of desalted H$_2$O and adjusted with dilute KOH, with stirring, to pH 2.8. After diluting the solution to 99 ml (ADP concentration 10%), approximately 100 ml of methanol is added, with stirring, at room temperature, the solution becoming slightly turbid. After about 30 minutes the crystallization of ADP-K starts, and is completed within one hour by the addition of another 50 ml of methanol. Then the mixture is let stand overnight at +4° C. in a refrigerator. After about 20 hours the crystallizate is removed with a suction filter, washed in some acetone, and vacuum dried without drying agent.

The yield amounts to about 11 g of ADP-K (95% of the theory).

EXAMPLE 2

5 g of crystallized ADP-K is dissolved in 55 ml of $H_2O$ (ADP-K concentration=9%) and about 50 ml of acetonitrile is added, with stirring, at room temperature. After about two hours the crystallization of ADP-K begins. To complete the crystallization, approximately 10 more milliliters of acetonitrile are added and the suspension is then placed, without stirring, in the refrigerator at +4° C. After about 20 hours the crystallizate is removed with a suction filter, washed in some acetone, and vacuum dried without drying agent.

The yield is about 4.5 g of ADP-K (90% of the theory).

EXAMPLE 3

40 ml of dioxane is added, with stirring, to 55 ml of a 9% ADP-K solution. After about one hour crystallization of ADP-K begins. To complete the crystallization, the suspension is let stand for 20 hours without stirring, at +4° C. Then the crystallizate is removed with a suction filter, washed in a little acetone, and vacuum dried without drying agent.

The yield is about 4.6 g of ADP-K (93% of the theory).

EXAMPLE 4

100 ml of a 10% ADP-K solution is treated by adding about 80 ml of acetone, with stirring, until the onset of turbidity. After about 6 hours, ADP-K begins to crystallize. Then the suspension is let stand at +4° C. without stirring. After about 20 hours an additional 20 ml of acetone is added and then the crystallizate is removed with a suction filter, washed in a little acetone and vacuum dried without drying agent.

The yield is about 8.7 g of ADP-K (87% of the theory).

EXAMPLE 5

2 g of ADP as free acid is dissolved in 10 ml of $H_2O$. Then 350 mg of KCl, dissolved in a little water, is added, with stirring. After about 15 minutes crystallization of ADP-K begins, ending about one hour later.

The crystallizate is removed with a suction filter, washed in a little methanol and acetone, and vacuum dried without drying agent.

The yield is about 2 g of ADP-K (85% of the theory).

It will be understood that the specification and examples are illustrative, but not limitative of the present invention and that other embodiments within the spirit and scope of the invention will suggest themselves to those skilled in the art.

What is claimed is:

1. Orthorhombic potassium salt of adenosine-5'-diphosphoric acid with the space group $P2_12_12$ and the elemental cell constants $a = 28.53 \pm 0.03$ Å

$b = 10.49 \pm 0.02$ Å

$c = 6.33 \pm 0.02$ Å

$\alpha = \beta = \gamma = 90.0°$

Volume = 1894.4 Å$^3$.

* * * * *